United States Patent [19]

Kröck et al.

[11] 4,422,973

[45] Dec. 27, 1983

[54] PROCESS FOR THE PREPARATION OF 1,4-DIAMINO-2,3-DICYANO-ANTHRAQUINONE

[75] Inventors: Friedrich W. Kröck, Cologne; Rütger Neeff, Leverkusen, both of Fed. Rep. of Germany

[73] Assignee: Bayer Aktiengesellschaft, Leverkusen, Fed. Rep. of Germany

[21] Appl. No.: 225,544

[22] Filed: Jan. 15, 1981

[30] Foreign Application Priority Data

Feb. 1, 1980 [DE] Fed. Rep. of Germany ....... 3003656

[51] Int. Cl.³ ............................................. C07C 97/24
[52] U.S. Cl. ..................................... 260/382; 260/378
[58] Field of Search ........... 260/382, 378, 371, 465 R, 260/465 D, 465 E, 465 H

[56] References Cited

U.S. PATENT DOCUMENTS

| 1,586,911 | 6/1926 | Moser | 260/382 |
| 1,938,029 | 12/1933 | Kugel | 260/378 |
| 2,496,414 | 2/1950 | Seymour et al. | 260/378 |
| 2,587,002 | 7/1952 | Seymour et al. | 260/378 |
| 3,234,242 | 2/1966 | Jost et al. | 260/367 |
| 4,294,769 | 10/1981 | Krock et al. | 260/378 |

FOREIGN PATENT DOCUMENTS 1142174 1/1963 Fed. Rep. of Germany .
1155786 10/1963 Fed. Rep. of Germany .

OTHER PUBLICATIONS

Methoden Der Organischen Chemie (Houben–Weyl), Muller & Bayer, Band VII/3c, 1979.
Chemical Abstract, vol. 72, #56697m "1-Aminoanthraquinone", 1969.

Primary Examiner—Delbert E. Gantz
Assistant Examiner—Raymond Covington
Attorney, Agent, or Firm—Sprung, Horn, Kramer & Woods

[57] ABSTRACT 1,4-Diamino-2,3-dicyano-anthraquinone is obtained in good yields and in high purity by reacting 1-amino-4-bromo-anthraquinone-2-sulphonic acid with ammonia and then reacting the 1,4-diamino-anthraquinone-2-sulphonic acid, which is not isolated as an intermediate, with cyanide ions, in formamide or N-methylformamide.

10 Claims, No Drawings

PROCESS FOR THE PREPARATION OF 1,4-DIAMINO-2,3-DICYANO-ANTHRAQUINONE

The subject of the invention is a process for the preparation of 1,4-diamino-2,3-dicyano-anthraquinone

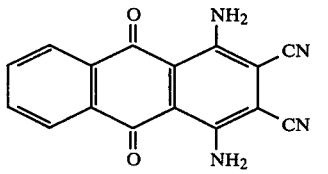

(I)

by reacting 1-amino-4-bromo-anthraquinone-2-sulphonic acid, or its salts, with ammonia and then reacting the resulting 1,4-diamino-anthraquinone-2-sulphonic acid, or its salts, with compounds which yield cyanide ions.

It is already known to prepare 1,4-diamino-anthraquinone-2-sulphonic acid, or its salts, by reacting 1-amino-4-bromo-anthraquinone-2-sulphonic acid, or its salts, with aqueous ammonia, in the presence of copper or copper salts, or with liquid ammonia, at 60° to 100° C. under a pressure at which liquid ammonia is still present, in the presence of copper, copper oxide or copper salts (German Patent Specification Nos. 1,142,174 and 1,155,786). The first-mentioned process in aqueous ammonia gives a very impure 1,4-diamino-anthraquinone-2-sulphonic acid because 1-amino-4-hydroxy-anthraquinone-2-sulphonic acid, which can only be separated off with great difficulty, is formed in a substantial amount as a by-product (German Patent Specification No. 1,142,174). The other process variant exhibits the disadvantage that it is carried out with liquid ammonia, without another solvent, in the region of the critical temperature of ammonia. This can result in severe complications, in particular on a large industrial scale, due to produce deposition on the vessel walls and overheating.

It is also known to prepare 1,4-diamino-2,3-dicyano-anthraquinone (I) by reacting 1,4-diamino-anthraquinone-2-sulphonic acid, or its salts, with compounds which yield cyanide ions, in an aqueous medium (German Patent Specification No. 536,998=U.S. Pat. No. 1,938,029). This process was later improved by carrying out the reaction in the presence of air or other oxidising agents and/or heavy metal catalysts (compare German Patent Specification No. 1,108,704=British Patent Specification No. 901,059, German Patent Specification No. 1,906,834=British Patent Specification No. 1,212,846 and U.S.S.R. Patent Specification No. 148,066). On subsequent treatment of the mixture resulting from the reaction of 1,4-diamino-anthraquinone-2-sulphonic acid with compounds which yield cyanide ions, in water, in accordance with these improved processes, it was never possible to achieve the proposed high yields of pure 1,4-diamino-2,3-dicyano-anthraquinone (I); as a result of incomplete exchange reactions or partial redissociation reactions (compare Houben-Weyl, Volume 7, Part 3 c, page 239), the reaction products obtained always contained relatively large amounts of 1,4-diamino-2-cyano-anthraquinone, which is not very easy to separate off, at least on an industrial scale.

In this state of the art, it is not possible to combine the two reaction steps to give a "one-pot process" in aqueous solution because the separate reaction steps in water already proceed insufficiently smoothly. However, a "one-pot process" would be desirable, not least because, due to its good solubility in water and other solvents, the isolation of the 1,4-diamino-anthraquinone-2-sulphonic acid is not without problems.

The object of the present invention was therefore to prepare the compound of the formula I in high yields, and in particular in high purity, from 1-amino-4-bromo-anthraquinone-2-sulphonic acid, or its salts, in accordance with the simplest possible process.

This object is achieved, according to the invention, by carrying out the reaction of 1-amino-4-bromo-anthraquinone-2-sulphonic acid, or its salts, with ammonia, in formamide or N-methylformamide, in the presence of copper, copper oxides and/or copper salts and, if appropriate, in the presence of acid-binding agents, under pressure, and treating the reaction mixture, after separating off the excess ammonia, with compounds which yield cyanide ions, preferably in the presence of an oxidising agent and, if appropriate, in the presence of acid-binding agents.

It is exceptionally surprising to note that the reaction of 1-amino-4-bromo-anthraquinone-2-sulphonic acid with ammonia, in the solvents to be used according to the invention, in particular formamide, proceeds so homogeneously and smoothly to give 1,4-diamino-anthraquinone-2-sulphonic acid, without the solvent entering into the reaction, and it is likewise surprising that the further reaction with compounds which yield cyanide ions, in these solvents, can be carried out so smoothly, because, in other solvents commonly used in industry, such as, for example, water, dimethylformamide, N-methylpyrrolidone, dimethylsulphoxide, sulpholan, pyridine, ethylene glycol, diethylene glycol, dimethylacetamide, tetramethylurea and the like, the yields are substantially lower under comparable reaction conditions.

The amount of the solvents to be employed according to the invention can vary within relatively wide limits and substantially depends on the solubility of the reactants. In any case, the system formed should be easy to stir and the starting materials should preferably dissolve completely therein. In general, 1 to 5 kg of solvent per mol of 1-amino-4-bromo-anthraquinone-2-sulphonic acid are required for this purpose.

1-Amino-4-bromo-anthraquinone-2-sulphonic acid and its salts, in particular the sodium salt, are large-scale industrial products.

In the reaction with ammonia, suitable copper catalysts, apart from finely divided copper metal (so-called copper-bronze), are Cu(I) oxide, Cu(II) oxide and copper salts, such as, for example, copper carbonate, basic copper carbonate, copper acetate, basic copper acetate, copper formate, copper(I) chloride, copper(II) chloride, copper(II) sulphate, copper(I) bromide, copper(II) bromide and the like.

The amount of ammonia which is required per mol of 1-amino-4-bromo-anthraquinone-2-sulphonic acid to be reacted can vary between 100 and 1,000 g, an amount of 200 to 500 g being preferred.

Sodium carbonate, sodium bicarbonate, potassium carbonate, sodium acetate or potassium acetate, in particular, can be added, if appropriate, as suitable acid-binding agents, the amount of the acid-binding agent added preferably being equivalent to the amount of HBr to be split off.

The reaction is carried out at 50° to 100° C. under the maximum autogenous pressure of 30 bars. The reaction time is about 1 to 10 hours. Thereafter, excess ammonia is distilled off and extensively removed, if appropriate by applying a slight vacuum. The 1,4-diaminoanthraquinone-2-sulphonic acid formed is processed further in solution. With the aid of thin layer chromatography, the reaction mixture is monitored for completion of the reaction.

Suitable oxidising agents for the subsequent reaction are both inorganic oxidising agents, such as air, oxygen, nitrites, nitrates, sodium chlorite, potassium bromate, ammonium persulphate and hydrogen peroxide and its addition compounds, such as sodium percarbonate, sodium perborate and sodium perpyrophosphate, and also organic oxidising agents, such as, for example, the urea/hydrogen peroxide addition compound, nitrobenzene, nitromethane, m-nitrobenzoic acid and its salts and m-nitrobenzenesulphonic acid and its salts. Nitromethane, nitrobenzene, m-nitro-benzenesulphonic acid and its salts, and also oxygen, advantageously in the form of atmospheric oxygen, are preferably used, if appropriate in the presence of catalytically active compounds, such as ammonium molybdate, ammonium vanadate or copper compounds, for example copper acetate.

Between 0.2 and 2 mols of nitrobenzene or m-nitrobenzene-sulphonic acid, if appropriate in the form of one of its salts, are preferably used per mol of the 1,4-diamino-anthraquinone-2-sulphonic acid to be reacted. The amount of the other oxidising agents indicated is determined according to their redox equivalents. In this process, a deficiency of oxidising agent is to be avoided because of the formation of by-products, and a relatively large excess is likewise to be avoided because of its interaction with the cyanide ions (compare British Patent Specification No. 901,059). However, in contrast to the data in the said patent, which relate to aqueous reaction media, it is not necessary in the present case, when using formamide or N-methyl-formamide, to meter the oxidising agent in during the reaction; it can be added at the start in the optimum amount to be determined by experiment.

Suitable acid-binding agents are, in particular, those which have already been mentioned above. The amount thereof depends mainly on the form in which the compound which yields cyanide ions is employed, and also on the amount already added in the first step. If anhydrous hydrocyanic acid is used, it is advantageous to add at least the equivalent amount of an acid-binding agent. An excess of acid-binding agent does not have an adverse influence on the reaction.

Suitable compounds which yield cyanide ions are, in particular, alkali metal and alkaline earth metal cyanides, such as sodium cyanide, potassium cyanide or magnesium cyanide, and also ammonium cyanide, zinc cyanide, copper(I) cyanide, complex copper cyanides and zinc cyanides, hydrocyanic acid, cyanohydrins of aldehydes and ketones, and the like. Sodium cyanide and potassium cyanide are preferred. The amount of the compound which yields cyanide ions is to be determined so that at least 2 mols, advantageously 2.5 to 10 mols, are employed per mol of the 1,4-diamino-anthraquinone-2-sulphonic acid or of the 1-amino-4-bromo-anthraquinone-2-sulphonic acid, or its salts, employed.

The reaction temperatures can vary within relatively wide limits, that is to say between 40° and 200° C. In general, the reaction is carried out in the temperature range which is customary for this type of synthesis, namely between 60° and 120° C.

The reaction has ended when the thin layer chromatogram indicates the total conversion of the starting material. This is generally the case after 2 to 20 hours and depending on the ratios of amounts employed and on the temperature. With optimum metering and at a temperature of 80° C., the reaction has normally ended after 4 hours. Working-up is very easy because, in contrast to the starting materials, the dinitrile (I) is extremely sparingly soluble in formamide, crystallises out during the reaction in a form which can readily be filtered off, and can thus easily be isolated by filtration.

The solvent can be recovered from the filtrate by simple distillation, whereupon the process is not only economical but also avoids sewage problems.

The reaction products are obtained directly in high purity (less than 3% of 1,4-diamino-2-cyano-anthraquinone), which is very important for their use as starting materials for the preparation of valuable dye-stuffs (compare U.S. Pat. No. 2,628,963), because relatively large contents of 1,4-diamino-2-cyano-anthraquinone shift the brilliant greenish-blue colour shade towards less desirable reddish shades.

It is to be regarded as a further advantage of the new process of preparation that the use of the solvents according to the invention makes it possible to reduce the amount of solvent to the extent that the space-time yield, compared with the known processes using water as the solvent, can be increased by a factor of about ten.

EXAMPLE 1

336.2 g of the Na salt of 1-amino-4-bromo-anthraquinone-2-sulphonic acid (85.2% pure, based on the free acid), 15 g of dry sodium carbonate and 5 g of anhydrous copper sulphate are introduced into 1.5 liters of formamide which is initially placed in a 3-liter stirred autoclave. The autoclave is closed and 350 cm$^3$ of liquid ammonia (measured under pressure at 20° C.; corresponding to 213.5 g) are introduced under pressure. The mixture is heated for 8 hours at 80° C., whilst stirring. Pressure: about 6.2 bars. (The pressure drops somewhat in the course of the reaction). The mixture is then left to cool, the pressure in the autoclave is let down and excess ammonia is removed by applying a vacuum for half an hour at 40° C. A thin layer chromatogram is prepared in order to confirm that the 1-amino-4-bromo-anthraquinone-2-sulphonic acid has been completely converted.

110.3 g of sodium cyanide, 45 g of nitrobenzene, 15 g of dry sodium carbonate and 300 cm$^3$ of formamide are added to the solution of 1,4-diamino-anthraquinone-2-sulphonic acid thus obtained, and the mixture is heated in an open vessel at 80° C., whilst stirring, until the intermediate has been totally converted. This is the case after at most 4 hours.

The reaction product which has crystallised out is filtered off whilst still hot, washed with 250 cm$^3$ of formamide and then rinsed with 500 cm$^3$ of methanol and sufficient hot water to make the effluent virtually colourless. About 2–3 liters of water are required for this purpose. After drying at 60° C., 195 g of a dark blue, crystalline product are obtained, which, according to analysis, contains 88.8% of 1,4-diamino-2,3-dicyano-anthraquinone and 1.3% of 1,4-diamino-2-cyano-anthraquinone. This corresponds to a yield of 80.1% of pure dicyano compound.

The formamide can be recovered from the mother liquor by distillation and then employed again for the reaction. In place of sodium carbonate, corresponding amounts of sodium bicarbonate, potassium carbonate, sodium acetate or potassium acetate, for example, can also be used in the reaction with equal success. Likewise, the anhydrous copper sulphate used as the catalyst in the reaction of 1-amino-4-bromo-anthraquinone-2-sulphonic acid with ammonia can also be replaced by the same amount of copper acetate or Cu(I) chloride, and equally smooth reactions can be achieved. The same effect is also achieved using copper carbonate, basic copper carbonate, basic copper acetate, copper formate, copper(II) chloride, copper(I) bromide, copper(II) bromide, copper(I) oxide, copper(II) oxide or finely divided copper metal (so-called copper-bronze).

EXAMPLE 2

336.2 g of the Na salt of 1-amino-4-bromo-anthraquinone-2-sulphonic acid (85.2% pure, based on the free acid) and 5 g of copper(I) chloride are introduced into 1.5 liters of formamide which is initially placed in a 3-liter stirred autoclave. The autoclave is closed and 350 cm$^3$ of liquid ammonia (measured under pressure at 20° C.; corresponding to 213.5 g) are introduced under pressure. The mixture is heated for 8 hours at 80° C., whilst stirring. Pressure: about 6.4 bars, dropping by about 1 bar in the course of the reaction. The mixture is then left to cool, the pressure in the autoclave is let down and excess ammonia is removed by applying a vacuum for half an hour at 40° C. A thin layer chromatogram is prepared in order to confirm that the conversion is complete.

110.3 g of sodium cyanide, 15 g of dry sodium bicarbonate, 109.8 g of dry sodium m-nitro-benzenesulphonate and 300 cm$^3$ of formamide are added to the resulting reaction solution, and the mixture is heated in an open vessel at 80° C., whilst stirring, until, after about 4 hours, the intermediate has been completely converted.

The reaction product which has crystallised out is filtered off, washed and dried as described in Example 1. This yields 191 g of a dark blue, crystalline product which, according to analysis, contains 88.1% of 1,4-diamino-2,3-dicyano-anthraquinone and 0.9% of 1,4-diamino-2-cyano-anthraquinone. The yield of pure dicyano compound is 77.9%.

In place of sodium cyanide, the corresponding amounts of the following compounds which yield cyanide ions can also be employed with the same success: potassium cyanide, magnesium cyanide, zinc cyanide or ammonium cyanide.

EXAMPLE 3

If Example 2 is repeated and the sodium cyanide in the second step is replaced by 192 g of acetone cyanohydrin and a further 120 g of dry sodium carbonate are also added, 185 g of a dark blue, crystalline product are obtained, which, according to analysis, contains 88.0% of 1,4-diamino-2,3-dicyano-anthraquinone and 1.3% of 1,4-diamino-2-cyano-anthraquinone. The yield of pure dicyano compound is 75.3%.

Acetone cyanohydrin can also be replaced by the corresponding amount of anhydrous hydrocyanic acid with similar success. Likewise, copper(I) cyanide and zinc cyanide, and the complex copper cyanides and zinc cyanides, such as, for example, potassium tetracyanocuprate(II), can also be employed as compounds which yield cyanide ions.

EXAMPLE 4

112.1 g of the Na salt of 1-amino-4-bromo-anthraquinone-2-sulphonic acid (85.2% pure, based on the free acid) and 2 g of copper acetate are introduced into 500 cm$^3$ of formamide which is initially placed in a 1-liter stirred autoclave. The autoclave is closed and 100 cm$^3$ of liquid ammonia (measured under pressure at 20° C.; corresponding to 61.0 g) are introduced under pressure. The mixture is heated for 8 hours at 80° C., whilst stirring. Pressure: 5.3 bars, dropping somewhat in the course of the reaction. The mixture is then left to cool, the pressure is let down and excess ammonia is removed by applying a vacuum for half an hour at 40° C. A thin layer chromatogram is prepared in order to confirm that the conversion is complete. 7.6 g of nitromethane, 36.8 g of sodium cyanide, 10.6 g of sodium carbonate and 100 cm$^3$ of formamide are added to the resulting reaction solution, and the mixture is heated in an open vessel at 80° C., whilst stirring, until, after about 8 hours, the intermediate has been completely converted.

The reaction product which has crystallised out is filtered off, washed and dried as described in Example 1. This yields 60.5 g of a dark blue, crystalline product which, according to analysis, contains 87.3% of 1,4-diamino-2,3-dicyano-anthraquinone and 1.1% of 1,4-diamino-2-cyano-anthraquinone. The resulting yield of pure dicyano compound is 73.3%.

In place of nitromethane, it is also possible to employ corresponding amounts of the following oxidising agents with similar success: nitrobenzene, sodium 3-nitro-benzoate, sodium nitrite and sodium nitrate. Similar results are also obtained when the following are employed as oxidising agents: sodium chlorite, potassium bromate, ammonium persulphate, potassium persulphate, hydrogen peroxide, sodium percarbonate, sodium perborate, sodium perpyrophosphate, peracetic acid or the urea/hydrogen peroxide addition compound.

EXAMPLE 5

87.3 g of the Na salt of 1-amino-4-bromo-anthraquinone (87.5% pure, based on the free acid) and 1.4 g of anhydrous copper sulphate are introduced into 400 cm$^3$ of formamide which is initially placed in a 1-liter stirred autoclave. The autoclave is closed and 80 cm$^3$ of liquid ammonia (measured under pressure at 20° C.; corresponding to 49 g) are introduced under pressure. The mixture is heated for 8 hours at 80° C., whilst stirring. Pressure: 4.5 bars, dropping somewhat in the course of the reaction. The mixture is then left to cool, the pressure in the autoclave is let down and a thin layer chromatogram is prepared in order to confirm that the conversion is complete.

29.4 g of sodium cyanide, 16.4 g of dry sodium acetate, 1.36 g of ammonium vanadate and 80 cm$^3$ of formamide are added to the resulting reaction solution, and the mixture is heated at 80° C., whilst passing through 12.8 liters of air/hour, until, after about 2.5 hours, the intermediate (1,4-diaminoanthraquinone-2-sulphonic acid) has been completely converted.

The reaction product which has crystallised out is filtered off, washed and dried as described in Example 1. This yields 48 g of a dark blue, crystalline product which, according to analysis, contains 87.6% of 1,4-diamino-2,3-dicyano-anthraquinone and 0.9% of 1,4-diamino-2-cyano-anthraquinone. This corresponds to a yield of 73% of pure dicyano compound.

In place of ammonium vanadate, 1.4 g of ammonium molybdate or 1.0 g of copper acetate can be employed as the catalyst with the same success.

EXAMPLE 6

109.1 g of the Na salt of 1-amino-4-bromo-anthraquinone-2-sulphonic acid (87.5% pure, based on the free acid), 5 g of dry sodium carbonate and 2 g of anhydrous copper sulphate are introduced into 500 cm$^3$ of N-methyl-formamide which is initially placed in a 1-liter stirred autoclave. The autoclave is closed and evacuated and 120 cm$^3$ of liquid ammonia (measured under pressure at 20° C.; corresponding to 73.2 g) are introduced under pressure. The mixture is heated for 8 hours at 80°–85° C., whilst stirring. Pressure: 6.2 bars, dropping somewhat in the course of the reaction. The mixture is then left to cool, the pressure is let down and excess ammonia is removed by applying a vacuum for half an hour at 40° C. A thin layer chromatogram is prepared in order to confirm that the reaction is complete.

48.8 g of potassium cyanide, 20 g of nitrobenzene, 20 g of sodium acetate and 100 cm$^3$ of N-methylformamide are added to the resulting reaction solution, and the mixture is heated at 80°–85° C., whilst stirring, until, after about 8 hours, the intermediate has been totally converted according to thin layer chromatography. The reaction mixture is worked up as described in Example 1. After drying, 66 g of a dark blue, crystalline product are obtained, which, according to analysis, contains 85.9% of 1,4-diamino-2,3-dicyano-anthraquinone and no 1,4-diamino-2-cyano-anthraquinone. This corresponds to a yield of 78.7% of pure product.

We claim:

1. A process for the preparation of 1,4-diamino-2,3-dicyano-anthraquinone comprising in a first step reacting 1-amino-4-bromo-anthraquinone-2-sulphonic acid, or its salts, with ammonia in formamide or N-methyl-formamide as a solvent and thereafter, without isolation, in a second step reacting the resulting product with compounds which yield cyanide ions.

2. Process of claim 1 wherein formamide is used as the solvent.

3. Process of claim 1 wherein the first reaction step with ammonia is carried out in the presence of copper sulphate, copper acetate or copper (I) chloride as catalysts.

4. The process of claim 1 wherein the second step is carried out in the presence of an oxidizing agent, a heavy metal catalyst and an acid binding agent.

5. Process of claim 4 wherein the second reaction step with compounds which yield cyanide ions is carried out in the presence of an oxidizing agent.

6. Process of claim 4 wherein air, oxygen, nitrobenzene or 3-nitro-benzene-sulphonic acid or its salts respectively is used as the oxidizing agent.

7. Process of claim 5 wherein air or oxygen is used as the oxidizing agent, in the presence of heavy metal catalysts selected from the group consisting of vanadates, molybdates and copper salts.

8. Process of claim 5 wherein nitrobenzene is used as the oxidizing agent.

9. Process of claim 1 wherein alkali metal or alkaline earth metal cyanides are used as the compounds which yield cyanide ions.

10. Process of claim 1 wherein sodium cyanide or potassium cyanide are used as the compounds which yield cyanide ions.

* * * * *